United States Patent [19]
Müller et al.

[11] Patent Number: 5,977,362
[45] Date of Patent: Nov. 2, 1999

[54] PROCESS FOR THE PREPARATION OF QUINAZOLINE-2,4-DIONES

[75] Inventors: Nikolaus Müller, Monheim; Klaus-Christian Paetz, Burscheid; Wolfgang Kiel, Odenthal, all of Germany

[73] Assignee: Bayer Aktiengesellschaft, Leverkusen, Germany

[21] Appl. No.: 09/084,695

[22] Filed: May 26, 1998

Related U.S. Application Data

[63] Continuation of application No. 08/516,057, Aug. 17, 1995, abandoned.

[30] Foreign Application Priority Data

Aug. 24, 1994 [DE] Germany .............................. 44 29 978

[51] Int. Cl.$^6$ ............................................... C07D 239/72
[52] U.S. Cl. ................................................................ 544/285
[58] Field of Search ............................................... 544/285

[56] References Cited

U.S. PATENT DOCUMENTS

| | | | |
|---|---|---|---|
| 4,287,341 | 9/1981 | Hess et al. | 544/285 |
| 4,405,623 | 9/1983 | Ishikawa et al. | 424/251 |
| 4,639,518 | 1/1987 | Bandurco et al. | 544/285 |
| 5,539,114 | 7/1996 | Cosmo et al. | 544/285 |

FOREIGN PATENT DOCUMENTS

| | | | |
|---|---|---|---|
| 0040793 | 12/1981 | European Pat. Off. | C07D 239/96 |
| 0176333 | 4/1986 | European Pat. Off. | C07D 239/96 |
| 0183458 | 6/1986 | European Pat. Off. | C07D 403/04 |
| 0260817 | 3/1988 | European Pat. Off. | C07D 471/04 |
| 0360417 | 3/1990 | European Pat. Off. | C07C 233/81 |
| 0545206A1 | 6/1993 | European Pat. Off. | C07D 239/54 |
| 0653423A1 | 5/1995 | European Pat. Off. | C07D 239/96 |
| 3712782A1 | 11/1988 | Germany | C07D 239/55 |
| 1059271 | 2/1987 | United Kingdom | 4882 64 |

OTHER PUBLICATIONS

A. Lespagnol, et al., "Dérivés de la benzoylène–urée(*)" Eur. J. Med. Chem., vol. 9, No. 3, pp. 263–268 (May–Jun. 1994).

Chemical Abstracts, vol. 83, p. 596, abstract No. 97348u, (1975).

E. Papadopoulos et al., "Convenient Preparation of N–Substituted 2–Amino–4H–3,1–benzoxazin–4–ones and 3–Substituted 2,4(1H,3H)–Quinazolinediones" J. Heterocyclic Chem., vol. 19, Mar./Apr. 1982, pp. 269–272.

J. Melendez, et al., "Synthesis of 3–Aryl–2,4–dioxo–1,2,3,4–tetrahydroquinazolines and 2–Arylamino–4–oxo–4H–3,1–benzoxazines from Methyl N–Aryldithiocarbamates", Synthesis, pp. 406–408 (1983).

Papadopoulos et al. J. Heterocyclic Chem., vol. 19, No. 269, pp. 269–272, 1982.

*Primary Examiner*—John M. Ford
*Attorney, Agent, or Firm*—Sprung Kramer Schaefer & Briscoe

[57] ABSTRACT

Quinazoline-2,4-diones are obtained in high yields and purities by reacting anthranilic acids with isocyanates and then, without isolation of the urea formed as intermediate, treating the reaction mixture with acid.

11 Claims, No Drawings

PROCESS FOR THE PREPARATION OF QUINAZOLINE-2,4-DIONES

This application is a continuation of application Ser. No. 08/516,057, filed Aug. 17, 1995, now abandoned.

The present invention relates to an improved process for the preparation of quinazoline-2,4-diones.

Processes for the preparation of quinazoline-2,4-diones are already known. Thus, substituted or unsubstituted anthranilic acids can be reacted with an isocyanate to give a derivative in which the amino group of the anthranilic acid has become part of the urea and this urea can be cyclized in the presence of ethanol with elimination of water (EP-A1 183 458). It is a disadvantage of this process that it must be carried out in two separate stages with intermediate isolation of the urea, because the preparation of the urea and the cyclization proceed in different solvents (see Example 2 of EP-A 1 183 458).

In order to prepare quinazoline-2,4-diones, alkali metal salts of anthranilic acid can also be reacted with dithiocarbamates (see Synthesis 1983, 406). A disadvantage in this process is the release of readily volatile organic sulphur compounds using the auxiliary mercury oxide. When this process is carried out industrially, particularly extensive expenditure for environmental protection measures is therefore necessary.

A process has now been found for the preparation of quinazoline-2,4-diones of the formula (I)

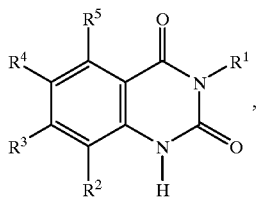

(I)

in which
 $R^1$ represents $C_6$–$C_{10}$-aryl which is unsubstituted or substituted by up to 5 halogen atoms and
 $R^2$, $R^3$, $R^4$ and $R^5$, independently of each other, each represent hydrogen, halogen, $C_1$–$C_6$-alkyl or $C_1$–$C_6$-alkoxy,
which is characterized in that an anthranilic acid of the formula (II)

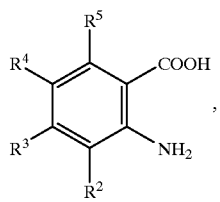

(II)

in which
 $R^2$, $R^3$, $R^4$ and $R^5$ have the meaning given under formula (I),
is reacted in an organic, aprotic solvent with an isocyanate of the formula (III)

$R^1$—N=C=O    (III), in which
 $R^1$ has the meaning given under formula (I),
and then, without isolation of the urea formed as an intermediate, the reaction mixture is treated with acid.

Halogen can denote fluorine, chlorine, bromine and/or iodine, preferably it denotes fluorine, chlorine or bromine.

In the formulae (I) and (II), preferably at least two of the radicals $R^2$ to $R^5$ represent hydrogen and preferably at most two represent fluorine, chlorine or bromine.

In the formulae (I) and (III), $R^1$ preferably represents phenyl which is preferably unsubstituted or substituted by 1 to 3 fluorine and/or chlorine atoms.

Particularly preferably, 2-amino-3-fluorobenzoic acid or 2-amino-5-fluorobenzoic acid and 2,4-dichlorophenyl isocyanate are used in the process according to the invention and 3-(2,4-dichlorophenyl)-8-fluoro-quinazoline-2,4-dione or 3-(2,4-dichlorophenyl)-6-fluoro-quinazoline-2,4-dione is prepared.

Anthranilic acids of the formula (II) are known compounds or are accessible by analogy with known compounds, for example by catalytic hydrogenation of the corresponding nitrobenzoic acids. Such nitrobenzoic acids can be prepared, e.g. in accordance with Tetrahedron Letters 40, 5115 (1988) or by analogy therewith.

The isocyanates of the formula (III) are likewise known compounds or are accessible by analogy with known compounds.

Based on 1 mol of anthranilic acid of the formula (II), for example, from 0.8 to 1.2 mol of an isocyanate of the formula (III) can be used. Preferably, equimolar amounts have been used.

Organic, aprotic solvents which can be used for the process according to the invention are, for example: esters such as methyl acetate and ethyl acetate, lactones such as butyrolactone, cyclic ethers such as tetrahydrofuran and dioxane, amides such as dimethylformamide and dimethylacetamide, lactams such as N-methylpyrrolidone, ketones such as acetone, methyl isobutyl ketone and cyclohexanone and aprotic organic sulphur compounds such as dimethyl sulphoxide and tetramethylene sulphone.

It is advantageous to carry out the process according to the invention using at least enough solvent so that the reaction mixture is always stirrable.

The temperature in the reaction of an anthranilic acid of the formula (II) with an isocyanate of the formula (III) can be, for example, between 0 and 200° C. It is preferably 20 to 150° C. If it is wished to avoid employing pressure, a solvent is used whose boiling point at atmospheric pressure is at or above the desired reaction temperature.

After the reaction between the anthranilic acid and the isocyanate has subsided, it is advantageous to stir the reaction mixture further, e.g. at 20 to 150° C., for some additional time, e.g. ½ to 5 hours.

It is an essential feature of the present invention that the addition of an acid proceeds without isolation of the urea formed as intermediate. Preferably, the acid is added to the same apparatus in which the reaction of the anthranilic acid with the isocyanate was performed.

Acids which are suitable are in particular strong organic and inorganic acids, such as sulphonic acids, sulphuric acid, hydrohalic acid and phosphoric acid. Preference is given to sulphuric acid and hydrochloric acid; particular preference is given to sulphuric acid. Preferably, the acids are used in semi-anhydrous or anhydrous form.

The acid can be used, e.g. in an amount from 0.2 to 5 mol, based on one mol of the isocyanate of the formula (III). Preferably, this amount is from 0.5 to 3 mol.

The action of the acid can proceed, for example, at temperatures from 0 to 200° C. and for a duration of 0.5 to 12 hours. Preference is given to temperatures from 20 to 150° C. and times of action of 1 to 8 hours.

After the action of the acid, the quinazoline-2,4-dione prepared is present in the reaction mixture. The reaction mixture can be worked up, e.g., by cooling it to room temperature, filtering it, washing the filter cake obtained with the solvent used and then drying it in vacuo at a moderately elevated temperature.

By means of the process according to the invention quinazoline-2,4-diones of the formula (I) can be obtained in high yields (e.g. virtually 90% of theory) and in high purities (e.g. greater than 98%). Further purification steps are not generally necessary.

This is particularly surprising, since in J. Heterocyclic Chem. 19, 269 (1982) it is described that the acidic condensation of 2-(3-arylureido)-benzoic acids leads to 3,1-benzoxazine-4-ones in good yields, while the action of an aqueous alcoholic sodium hydroxide solution results in quinazoline-2,4-diones in good yields.

EXAMPLES

Example 1

In a four-necked flask equipped with stirrer, reflux cooler, thermometer and dropping funnel, 31 g of 5-fluoroanthranilic acid were dissolved in 280 ml of ethyl acetate at 50° C. To this were added dropwise in the course of 20 minutes 37.6 g of molten 2,4-dichlorophenyl isocyanate from a heatable dropping funnel. The internal temperature increased to 65° C., at which the reaction mixture thickened, but still remained stirrable. It was further stirred for 2 hours under reflux, then cooled to 70° C. and 39.5 g of concentrated sulphuric acid were added dropwise in the course of 10 minutes. The internal temperature again increased to reflux temperature. At this temperature the mixture was further stirred for 4.5 hours, a readily stirrable suspension resulting. The mixture was then cooled to room temperature, the product filtered off by suction and washed twice on the filter each time using 75 ml of ethyl acetate. After drying, 59 g of 3-(2,4-dichlorophenyl)-6-fluoroquinazoline-2,4-dione were obtained having a melting point above 250° C., in a purity of 99% and in a yield of 89.8% of theory.

Example 2

Similarly to the procedure described in Example 1, 136 g of anthranilic acid and 188 g of 2,5-dichlorophenyl isocyanate were reacted in one litre of ethyl acetate to give the urea. 36.5 g of hydrogen chloride gas were introduced in the course of 1 hour into the boiling suspension of the (2-carboxyphenyl)-(2',5'-dichlorophenyl)-urea. The mixture was further stirred under reflux for 3 hours, cooled to room temperature and the product precipitated out was isolated by filtration. After drying, 285 g of pure 3-(2,5-dichlorophenyl)-quinazoline-2,4-dione were present having a melting point of 228 to 231° C. This corresponds to a yield of 93% of theory.

Example 3

42.5 g of 4-chloroanthranilic acid were dissolved in 250 ml of N-methylpyrrolidone and 29.5 g of phenyl isocyanate were added dropwise at room temperature in 30 minutes. The mixture was further stirred for 5 hours at 80° C. and then 24.5 g of concentrated sulphuric acid were added dropwise in the course of 1 hour. The mixture was then further stirred at 80° C. for 3 hours, then cooled to room temperature, 500 ml of water were added, the product precipitated out was filtered off by suction, washed with water and dried in a vacuum drying cabinet. In this manner 57.4 g (85% of theory) of pure 3-phenyl-7-chloro-quinazoline-2,4-dione were obtained having a melting point of above 300° C.

Example 4

21.6 g of 5-bromoanthranilic acid and 15.4 g of 4-chlorophenyl isocyanate were reacted in a similar procedure as described in Example 1 in 200 ml of butyl acetate at 100° C. and with a further stirring time of 4 hours. 18 g of hydrogen chloride gas were then introduced into the suspension of the urea formed in the course of 30 minutes and the mixture was then further stirred at 100° C. for 3 hours. For the work-up of the reaction mixture, sufficient butyl acetate was first distilled off at atmospheric pressure until a thick suspension had resulted, then 200 ml of water were added and the product precipitated out was filtered off. After drying, 31.5 g (90% of theory) of 6-bromo-3-(4-chlorophenyl)-quinazoline-2,4-dione were obtained having a melting point of 212–214° C. (decomposition).

What is claimed is:

1. A process for the preparation of a quinazoline-2,4-dione of the formula (I)

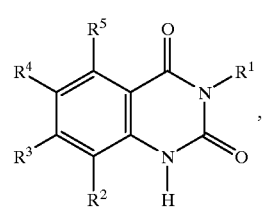

(I)

in which

R$^1$ represents C$_6$–C$_{10}$-aryl which is unsubstituted or substituted by up to 5 halogen atoms and R$^2$, R$^3$, R$^4$, and R$^5$, independently of each other, each represent hydrogen, halogen, C$_1$–C$_6$-alkyl or C$_1$–C$_6$-alkoxy, in which process an anthranilic acid of the formula (II)

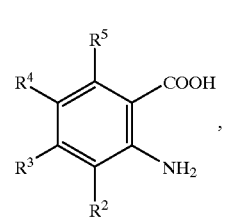

(II)

in which

R$^2$, R$^3$, R$^4$, and R$^5$ have the meaning given under formula (I), is reacted in an organic, aprotic solvent selected from the group consisting of esters, lactones, cyclic ethers, amides, lactams, ketones and aprotic organic sulphur compounds with an isocyanate of the formula (III)

(III)

in which
R¹ has the meaning given under formula (I), and then the resulting reaction mixture is treated with acid.

2. The process of claim 1, in which in the formulae (I) and (III) R¹ represents phenyl which is unsubstituted or substituted by 1 to 3 fluorine and/or chlorine atoms and in the formulae (I) and (II) at least two of the radicals R² to R⁵ represent hydrogen and at most two of these radicals represent fluorine, chlorine or bromine.

3. A process for the preparation of a quinazoline-2,4-dione of the formula (I)

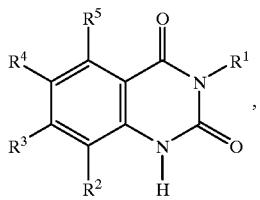
(I)

in which
R¹ represents $C_6$–$C_{10}$-aryl which is unsubstituted or substituted by up to 5 halogen atoms and
R², R³, R⁴, and R⁵, independently of each other, each represent hydrogen, halogen, $C_1$–$C_6$-alkyl or $C_1$–$C_6$-alkoxy,
in which process an anthranilic acid of the formula (II)

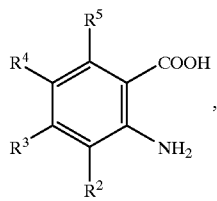
(II)

in which
R², R³, R⁴, and R⁵ have the meaning given under formula (I), is reacted in an organic, aprotic solvent selected from the group consisting of esters, lactones, cyclic ethers, amides, lactams, ketones and aprotic organic sulphur compounds with an isocyanate of the formula (III)

(III)

in which
R¹ has the meaning given under formula (I), and then, without isolation of the urea formed as an intermediate, the reaction mixture is treated with acid.

4. The process of claim 1, in which esters, lactones, cyclic ethers, amides, lactams, ketones or aprotic organic sulphur compounds are used as solvent.

5. The process of claim 1, in which the reaction of an anthranilic acid of the formula (II) with an isocyanate of the formula (III) is carried out at temperatures between 0 and 200° C.

6. The process of claim 1, in which, after the reaction between the anthranilic acid and the isocyanate has subsided, the mixture is stirred further at 20 to 150° C. for an additional ½ to 5 hours.

7. The process of claim 1, in which the acid used is a sulphonic acid, sulphuric acid, a hydrohalic acid or phosphoric acid.

8. The process of claim 1, in which the acid is allowed to act at temperatures from 0 to 200° C. and for a duration of 0.5 to 12 hours.

9. The process of claim 1, in which the reaction mixture present after the reaction is worked up by cooling it, filtering it, washing the filter cake obtained with the solvent used and then drying it in vacuo at an elevated temperature.

10. The process according to claim 1, wherein the organic, aprotic solvent is methyl acetate, ethyl acetate, butyrolactone, tetrahydrofuran, dioxane, dimethylformamide, dimethylacetamide, N-methylpyrrolidone, acetone, methyl isobutyl ketone, cyclohexanone, dimethyl sulphoxide or tetramethylene sulphone.

11. The process according to claim 1, wherein the acid is HCl or $H_2SO_4$.

* * * * *